(12) United States Patent
Maurer et al.

(10) Patent No.: US 10,814,054 B2
(45) Date of Patent: Oct. 27, 2020

(54) INTERMEDIATE ELEMENT FOR A MEDICAL EXTRACORPOREAL FLUID LINE, AND SYSTEM AND METHOD ASSOCIATED THEREWITH

(71) Applicant: Novalung GmbH, Heilbronn (DE)

(72) Inventors: Andreas Maurer, Tübingen (DE); Sven Filipon, Heilbronn (DE)

(73) Assignee: Novalung GmbH, Heilbronn (DE)

( * ) Notice: Subject to any disclaimer, the term of this patent is extended or adjusted under 35 U.S.C. 154(b) by 291 days.

(21) Appl. No.: 15/770,250

(22) PCT Filed: Oct. 20, 2016

(86) PCT No.: PCT/EP2016/075294
§ 371 (c)(1),
(2) Date: Apr. 23, 2018

(87) PCT Pub. No.: WO2017/068081
PCT Pub. Date: Apr. 27, 2017

(65) Prior Publication Data
US 2018/0303994 A1 Oct. 25, 2018

(30) Foreign Application Priority Data

Oct. 23, 2015 (EP) ..................... 15003041

(51) Int. Cl.
*A61M 1/16* (2006.01)
*G01N 33/49* (2006.01)
(Continued)

(52) U.S. Cl.
CPC ....... *A61M 1/1603* (2014.02); *A61B 5/14542* (2013.01); *A61B 5/14557* (2013.01);
(Continued)

(58) Field of Classification Search
CPC ............ A61B 5/14557; A61M 1/1698; A61M 1/3609; A61M 1/3673; A61M 2205/3303;
(Continued)

(56) References Cited

U.S. PATENT DOCUMENTS

| 3,418,853 A | 12/1968 | Curtis |
| 4,194,974 A | 3/1980 | Jonsson |

(Continued)

FOREIGN PATENT DOCUMENTS

| CN | 1913825 A | 2/2007 |
| CN | 101394879 A | 3/2009 |

(Continued)

OTHER PUBLICATIONS

Benchoff, B., "Injection Molding With Hot Glue", Hackaday, May 12, 2014, one page.

*Primary Examiner* — Leslie R Deak
(74) *Attorney, Agent, or Firm* — Dinsmore & Shohl LLP (57) ABSTRACT

An intermediate element for a medical extracorporeal fluid line designed to conduct a fluid, such as blood, has a main part extending between two connection parts. A flow channel passes continuously through the main part and the connection parts. The connection parts hydraulically connect the main body to a fluid line. On the periphery of the main part a receiving area is arranged, which is designed to receive a measurement value transmitter. An opening to the flow channel is defined in the receiving area and is sealed in a fluid-tight manner towards the receiving area by an elastic element. The measurement value transmitter is a gas sensor of a sensor device for measuring at least one gas contained in the fluid. The elastic element is a diffusion element, which is permeable to at least one gas. The diffusion element is bonded to an edge of the opening.

22 Claims, 4 Drawing Sheets

(51) Int. Cl.
　　*A61B 5/145*　　(2006.01)
　　*A61M 1/36*　　(2006.01)
　　*A61B 5/1455*　　(2006.01)
　　*A61B 5/00*　　(2006.01)

(52) U.S. Cl.
　　CPC ......... *A61B 5/6866* (2013.01); *A61M 1/1698* (2013.01); *A61M 1/367* (2013.01); *A61M 1/3609* (2014.02); *A61M 1/3673* (2014.02); *G01N 33/4925* (2013.01); *A61M 2205/0238* (2013.01); *A61M 2205/3303* (2013.01); *A61M 2205/3331* (2013.01); *A61M 2209/08* (2013.01); *A61M 2230/20* (2013.01); *A61M 2230/202* (2013.01); *A61M 2230/204* (2013.01); *A61M 2230/205* (2013.01)

(58) Field of Classification Search
　　CPC ...... A61M 2230/202; A61M 2230/205; G01N 33/4925
　　See application file for complete search history.

(56) References Cited

U.S. PATENT DOCUMENTS

| | | | |
|---|---|---|---|
| 4,263,808 A | | 4/1981 | Bellotti et al. |
| 4,425,918 A | | 1/1984 | Moll et al. |
| 4,431,009 A | | 2/1984 | Marino, Jr. et al. |
| 4,443,407 A | | 4/1984 | Weinberg et al. |
| 4,640,820 A | * | 2/1987 | Cooper .............. A61B 5/14539 210/232 |
| 4,734,184 A | | 3/1988 | Burleigh et al. |
| 4,924,872 A | | 5/1990 | Frank |
| 5,105,820 A | | 4/1992 | Moriuchi et al. |
| 5,148,811 A | | 9/1992 | Messinger |
| 5,237,999 A | | 8/1993 | von Berg |
| 5,351,686 A | | 10/1994 | Steuer et al. |
| 5,370,123 A | | 12/1994 | Shinzato |
| 5,387,329 A | | 2/1995 | Foos et al. |
| 5,421,208 A | | 6/1995 | Packard et al. |
| 5,581,038 A | | 12/1996 | Lampropoulos et al. |
| 5,607,645 A | | 3/1997 | Bentsen et al. |
| 5,614,677 A | | 3/1997 | Wamsiedler et al. |
| 5,641,458 A | * | 6/1997 | Shockley, Jr. ......... G01N 21/05 422/544 |
| 5,925,830 A | | 7/1999 | Schalk |
| 5,965,089 A | | 10/1999 | Jarvik et al. |
| 6,101,406 A | * | 8/2000 | Hacker .............. A61B 5/14557 356/39 |
| 6,136,136 A | | 10/2000 | Heider |
| 6,272,930 B1 | | 8/2001 | Crozafon et al. |
| 6,725,726 B1 | | 4/2004 | Adolfs et al. |
| 6,880,404 B2 | | 4/2005 | Uberreiter |
| 6,887,214 B1 | | 5/2005 | Levin et al. |
| 7,025,750 B2 | | 4/2006 | Brugger et al. |
| 7,059,195 B1 | | 6/2006 | Liu et al. |
| 7,108,672 B2 | | 9/2006 | Steele et al. |
| 7,313,968 B2 | | 1/2008 | Kaneko et al. |
| 7,410,473 B2 | | 8/2008 | Levin et al. |
| 7,748,275 B2 | | 7/2010 | Kouda et al. |
| 7,771,380 B2 | | 8/2010 | Jonsson et al. |
| 7,856,887 B2 | | 12/2010 | Klees et al. |
| 7,879,241 B2 | | 2/2011 | Sparks et al. |
| 7,921,723 B2 | | 4/2011 | Reiter et al. |
| 8,506,684 B2 | | 8/2013 | Weaver et al. |
| 8,721,883 B2 | | 5/2014 | Lauer |
| 9,186,072 B2 | | 11/2015 | Manstrom et al. |
| 9,551,625 B2 | | 1/2017 | Brugger et al. |
| 9,808,567 B2 | | 11/2017 | O'Mahony |
| 9,883,888 B2 | | 2/2018 | Frey et al. |
| 2002/0073782 A1 | | 6/2002 | Chevallet et al. |
| 2004/0039290 A1 | | 2/2004 | Narimatsu et al. |
| 2005/0284815 A1 | | 12/2005 | Sparks et al. |
| 2007/0261496 A1 | | 11/2007 | Jonsson et al. |
| 2010/0114063 A1 | | 5/2010 | Recinella et al. |
| 2012/0258545 A1 | | 10/2012 | Ash et al. |
| 2014/0076058 A1 | | 3/2014 | Brugger et al. |
| 2015/0082863 A1 | | 3/2015 | Sagebiel |

FOREIGN PATENT DOCUMENTS

| | | |
|---|---|---|
| CN | 103124519 A | 5/2013 |
| DE | 29810331 U1 | 9/1998 |
| DE | 102013012433 A1 | 1/2015 |
| EP | 0330891 A1 | 9/1989 |
| EP | 0688531 A1 | 12/1995 |
| EP | 0762084 A2 | 3/1997 |
| EP | 0993266 A1 | 4/2000 |
| JP | H03258235 A | 11/1991 |
| JP | 2005311321 A | 11/2005 |
| JP | 2008296061 A | 12/2008 |
| JP | 2009200172 A | 9/2009 |
| JP | 2011222782 A | 11/2011 |
| JP | 201432190 A | 2/2014 |
| WO | 1997015228 A1 | 5/1997 |
| WO | 2012127422 A1 | 9/2012 |

\* cited by examiner

INTERMEDIATE ELEMENT FOR A MEDICAL EXTRACORPOREAL FLUID LINE, AND SYSTEM AND METHOD ASSOCIATED THEREWITH

CROSS-REFERENCE TO RELATED APPLICATIONS

This application is the U.S. national stage of PCT/EP2016/075294 filed Oct. 20, 2016, which claims priority of European Patent Application 15003041.9 filed Oct. 23, 2015 of which is hereby incorporated by reference in its entirety.

FIELD OF THE INVENTION

The present invention relates to an intermediate element for a medical extracorporeal fluid line, which is designed to conduct a fluid, in particular blood, comprising a main part, which extends between connection parts, wherein a flow channel is passing continuously through the main part and the connection parts for conducting the fluid and wherein the connection parts are configured to connect the main part to a fluid line for conducting a fluid and wherein a receiving area is arranged on the periphery of the main part, which is configured to receive a measurement value transmitter, and wherein an opening to the flow channel is arranged on the receiving area in the main part, which is sealed by means of an elastic element to the receiving area in a fluid-tight way. In addition, the present invention relates to a medical extracorporeal fluid system, in particular a medical extracorporeal blood circulation having at least one fluid line, which is configured to conduct a fluid, in particular blood, having at least one introduction element, which is configured to conduct a fluid from a patient in the fluid line, and includes a gas exchange module, which is connected to the at least one fluid line for conducting a fluid. The present invention further relates to a method for measuring a gas contained in a fluid of a human or animal body, which is conducted in a medical extracorporeal fluid system, in particular a medical extracorporeal blood circulation.

The present invention relates in particular to an intermediate element comprising features described below, a medical extracorporeal fluid system, and a method.

BACKGROUND OF THE INVENTION

Intermediate elements for medical extracorporeal fluid lines are known, for example from systems for a medical extracorporeal lung support (ECLA/ILA). Such intermediate elements serve as connectors to connect fluid lines, for example tubing lines made of PVC, for example, or are configured as adapters, which serve to connect different kind of fluid lines or to connect said fluid lines to other components of the system. Further systems, in which for example such kind of intermediate elements are used, are systems for extracorporeal membrane oxygenation (ECMO), systems for pump-free arterio-venous lung support (PECLA), or systems for paracorporeal lung support (PLA). The field of applications of such systems comprise ARDS (adult respiratory distress syndrome), ALI (acute lung injury), kidney treatment, for patients having chronic respiratory distress syndrome (COPDP/AECOPD) and also in a lung replacement method during cardiac surgery, for example. A usage in the laboratory for a fast analysis of the parameters $CO_2$, $O_2$ is also conceivable.

In addition, such kind of intermediate elements are also used in systems for extracorporeal circulation support or extracorporeal life-support (ECLS). Field of applications of ECLS are, for example, patients having disease patterns in cardiology and cardiac surgery, for example, for patients having a decompensation of a cardiac insufficiency, where the function of the heart is no longer sufficient to supply the organism with oxygenated blood in an adequate way.

For such kind of systems, the blood provided to the system normally has to be taken in an expensive way by means of a port on the fluid line, and the amount of $O_2$ and $CO_2$ has to be evaluated in a blood gas analysis (BGA). This procedure needs a lot of time and is expensive. As an alternative, there is currently only the possibility to perform transcutaneous measurements of $CO_2/O_2$ on the skin of the patient. Hereto a measurement sensor has to be applied on the skin of the patient and a gap between the skin and the sensor has to be filled with a fluid in order to be able to perform the measurement at all. However, this method is also very expensive, as a calibration and a temperature control (41-43° C.) is required due to the microcirculation of the skin.

From DE 10 2013 012 433 A1 an arrangement for an extracorporeal circulation support is known, in which an extracorporeal blood circulation is performed from a venous cannula to an arterial cannula by means of an oxygenator, by adding oxygen to the blood and removing $CO_2$. A blood pump arranged in the extracorporeal blood circulation supplies blood via lines from the venous cannula to the arterial cannula. In this application a measurement of the amount of $O_2$ or $CO_2$ in the oxygenated blood is not described.

From WO 2012/127422 A1 a device for extracorporeal monitoring of physical-chemical blood parameters is known, which comprises an elongated body having an inlet and an outlet for organic fluid media. In the body a detection chamber between the inlet and the outlet is arranged through which the organic fluid is flowing. The body comprises at least a first casing for a first sensor element for sensing a pressure parameter of the fluid and at least a second casing for a second sensor element for sensing another parameter, which is different from the pressure parameter. For example, oxygen pressure sensors and $CO_2$ pressure sensors may be arranged on the casings. The sensor comprises a hydrophobic and elastically deformable membrane, which is designed to come into contact with the fluid to be monitored.

From WO 97/15228 A1, on which the present invitation is based, there is also known a plastic element, which is designed to connect two tubes. In an opening of the plastic element a flexible diaphragm is arranged, which seals the opening in the side wall of the plastic element in a fluid-tight way. A connection arm is located adjacent to the opening, in which a connection casing may be inserted, which includes a measurement value transmitter. In an inserted state, a gap filled with air is located between the measurement value transmitter and the flexible diaphragm. The arrangement is thus used to measure the blood pressure. However, said element is not suited to measure the gas concentration in a fluid.

SUMMARY OF THE INVENTION

It is an object of the present invention to provide an intermediate element for a medical extracorporeal fluid line, for which a fluid gas analysis, as for example a blood gas analysis (BGA), may be performed in an efficient way. It is a further object of the present invention to provide a medical extracorporeal fluid system, in particular a medical extracorporeal blood circulation, which enables an efficient fluid gas analysis, in particular an efficient blood gas analysis. It is further an object of the present invention to provide a method for measuring a gas contained in a human or animal bodily fluid conducted in a medical extracorporeal fluid system, which is easy to perform, and which eliminates the disadvantages of the known methods.

The present invention relates to an intermediate element for a medical extracorporeal fluid line, which is configured to conduct a fluid, in particular blood, including a main part, which extends between the connection parts, wherein a flow channel is continuously passing through the main part and the connection parts for conducting the fluid, and wherein the connection parts are configured to hydraulically connect the main part to a fluid line and wherein a receiving area is arranged on the periphery of the main part, which is configured to receive a measurement value transmitter and wherein an opening to the flow channel is arranged on the receiving area in the main part, which is sealed in a fluid-tight way towards the receiving area by means of an elastic element.

According to the invention, the receiving area may be configured in a way that it may receive a measurement value transmitter of a sensor device, which is designed as a gas sensor, for measuring at least one gas contained in the fluid, and wherein the elastic element is a diffusion element, which is permeable to at least one gas, wherein the diffusion element is bonded to an edge of the opening in the connection region. The edge may thus be formed as circumferential collar, for example, which is arranged around the opening on the main part in an annular shape. The diffusion element may here be connected to an annular zone, which is located radially outside, in a fluid-tight way by means of a welding or gluing method, for example.

Due to said measure, a gas sensor may be arranged on the intermediate element, by means of which a fluid gas analysis, in particular a blood gas analysis, may be performed, in case a fluid, in particular blood, flows through the flow channel in the intermediate element. Hereby, when an intermediate element according to the invention is used in medical extracorporeal fluid systems, as for example in medical extracorporeal blood circulations, an in-line blood gas analysis becomes possible, which is carried out in real time during operation of the system. This is of advantage for regulating/controlling a medical extracorporeal fluid system, as for example a medical extracorporeal blood circulation.

By using a gas-permeable diffusion element in the seam between the flow channel in the main part of the intermediate element and the receiving area for the gas sensor, a direct contact of the gas sensor with the fluid conducted in the flow channel is prevented, thus the gas sensor may be reused without expensive cleaning procedures. For example, a gas sensor may be used as gas sensor, which is suited e.g. for a transcutaneous measurement of $CO_2/O_2$.

In an advantageous development of the intermediate element, the diffusion element is configured as a diffusion film or foil. Regarding the production technique, such a diffusion film or foil may be easily cut into the desired shape and may be easily connected to the intermediate element. Here, the diffusion film or foil has preferably a rounded, in particular circular geometry, whereby asymmetric stresses and wrinklings may easily be prevented in the receiving area of the intermediate element during application of the diffusion film or foil. The diffusion film may also have a polygon geometry, in particular the shape of a n-cornered polygon, wherein n may preferably be in a range of between 3-∞.

In an advantageous development, the diffusion element or the diffusion film or foil is made of a material selected of the group of polymethyl-pentenes, preferably of poly-4-methyl-1-pentene. Said material is very permeable to gases like $CO_2$ or $O_2$, but absolutely fluid-tight, which prevents a leakage of blood or other bodily fluids through the diffusion element. Alternatively, also polypropylene may be used as material for the diffusion element or the diffusion film, for example, which also has excellent gas diffusion properties and is completely fluid-tight against fluids.

In addition, the wall delimiting the flow channel may be provided with a coating in order to prevent or inhibit coagulation and/or immune responses. The wall delimiting the flow channel may for example be coated with heparin, in particular with highly molecular heparin. Thereby the hemocompatability of the intermediate element is enhanced. For example, an albumin coating may also be provided in order to inhibit an immune response or other coatings, which will be available in the future.

In a further advantageous development, the diffusion element may have a coating at least on the side facing the flow channel in order to prevent or inhibit coagulation and/or immune responses. The diffusion element may for example be coated with heparin, in particular with highly molecular heparin, at least on the side facing the flow channel. Also, by means of this measure the hemocompatibility of the diffusion element and thus of the intermediate element is enhanced. For example, an albumin coating may also be provided in order to inhibit an immune response or other coatings, which will be available in the future.

In an advantageous development of the intermediate element according to the invention, the diffusion element, in particular the diffusion film or foil, is biased or prestressed towards the receiving area. The biasing or prestressing may be set from a man skilled in the art depending on that, whether the intermediate element including the sensor is arranged upstream or downstream of the gas exchange module or the oxygenator, or whether the intermediate element is arranged upstream or downstream of a pump, that is, whether an overpressure or a negative pressure is applied. By means of this measure it is realized that the gas sensor directly and seamlessly abuts on the diffusion element in the state arranged in the receiving area. Thus, no fluid has to be introduced between the diffusion element and the gas sensor.

As an alternative to biasing or prestressing the diffusion film or foil, the diffusion film or foil may also have a film or foil thickness, which is suited to arrange the diffusion film or foil only due to its internal stress as a completely flat element above the opening in the receiving area on the main part, onto which the gas sensor may abut seamlessly or without a gap at the side of the measurement. This would also eliminate the need of introducing a fluid between the diffusion element and the gas sensor.

In a further development of the invention, the transition of the diffusion element to the adjacent wall of the flow channel is formed in a way, which is smooth to fluids. That is, there are no or only minor edges or steps at the transition. Due to this design, turbulences, in particular for flow channel diameters or fluid line diameters of ⅜ inch or ¼ inch, may be prevented. Such kind of turbulences may otherwise lead to deposits, in particular blood clots.

A holding device may be provided on the main part of the intermediate element in the region of the receiving area, which is configured to set the gas sensor on the receiving area in a reversible way. Hereby, the gas sensor may be set on the intermediate element in a detachable way; and may also be easily removed from the intermediate element.

Preferably, the holding device on the intermediate element comprises at least one holder element, which is adapted to cooperate with a counter holder element of the gas sensor. In particular, the holder element may be brought into engagement with the counter holder element, so that the gas sensor may be set in the receiving area on the intermediate element in a detachable way.

The at least one holder element is thus preferably adapted as engagement hook, which is configured to cooperate with a counter holder element of the gas sensor, which is adapted as an engagement protrusion. Hereby, an engagement connection or snap connection may be created, by means of which the gas sensor may be reversibly fixed in the receiving area of the intermediate element in an uncomplicated way. For securely fixing the gas sensor in the receiving area of the intermediate element, the holding device may comprise a plurality of holder elements, which are arranged circumferentially around the receiving area. All or at least one of the holder elements may here be configured as engagement hook.

In an advantageous embodiment of the invention, the intermediate element including the diffusion element, which is arranged therein, is configured as disposable element or disposable product, which is designed for single use only. By means of said measure, an excellent hygienic solution may be provided, which intentionally avoids disinfection and cleaning of the intermediate element after usage, which is detrimental to the environment.

Such a disposable product may in particular be packaged in sterile safety packagings.

In addition, the present invention further relates to a medical extracorporeal fluid system, in particular a medical extracorporeal blood circulation having at least one fluid line, which is configured to conduct a fluid, in particular blood, having at least one introduction element, which is configured to conduct a fluid from a patient into the fluid line, and which comprises a gas exchange module, which is hydraulically connected to the at least one fluid line.

According to the invention, a fluid line is configured to be connected to an intermediate element according to the invention, so that the intermediate element is hydraulically interposed in the fluid line. That is, the fluid, which is conducted through the fluid line, is also passing through the intermediate element. Here the fluid, in particular blood, is passed next to the diffusion element and thus next to a gas sensor located in the receiving area, which may perform a fluid gas analysis, in particular blood gas analysis, in real time. The gained measurement data may thus be used as input parameters for creating the medical extracorporeal fluid system, in particular the medical extracorporeal blood circulation. Here, it may be advantageous, when a first fluid line, which is connected to the introduction element on the one hand and to the gas exchange module on the other hand, is adapted to be hydraulically connected to the intermediate element. Said first fluid line may be a first line, in particular, which contains blood, by means of which blood is taken from a patient and is transferred to a gas exchange module. Due to the possibility to arrange the intermediate element according to the invention including a gas sensor in said first fluid line, a gas analysis of the untreated fluid or blood, which has been taken from the patient, may be carried out.

Ideally, the first fluid line comprises two separate line portions, the ends thereof, which are opposite to the introduction element and the gas exchange module, are adapted for connection to the intermediate element. The two free ends of the two line portions of the first fluid line may thus be connected to a connection part of the intermediate element, respectively, so that the intermediate element may be hydraulically interposed in the fluid line.

In the application state of the medical extracorporeal fluid system, the intermediate element is hydraulically interposed in the first fluid line. In case the gas sensor is arranged on said intermediate element, then a fluid gas analysis or a blood gas analysis of the fluid or blood flowing through the first fluid line may be carried out.

The invention further provides a method for measuring a gas contained in a human or animal bodily fluid, which is conducted in a medical extracorporeal fluid system, in particular a medical extracorporeal blood circulation. In this method according to the invention, first an intermediate element according to the invention is hydraulically interposed in a fluid line of the medical extracorporeal fluid system. That is, by means of the two connection parts thereof, the intermediate element according to the invention is connected to the two free ends of the first fluid line, which comprises two line portions. Accordingly, a gas sensor of a sensor device is arranged on the receiving area of the intermediate element. Furthermore, the fluid of the patient is conducted into a first fluid line of the fluid system and returned to the patient by means of a further fluid line. Here, the fluid flows through a flow channel of the intermediate element, where it is passed next to the diffusion element, which abuts on the gas sensor, in particular on the sensor element of the gas sensor, on the side opposite to the flow channel. The gas sensor measures the partial pressure of at least one gas contained in the fluid, which is selected from the group of $O_2$, $CO_2$, $CO$, $N_2$. From the partial pressure data, the concentration of the gases in the fluid may be determined. By the method according to the invention, fluid gas data, in particular blood gas analysis data, may be retrieved in real time during operation time of the medical extracorporeal fluid system, and may be directly used for setting the medical extracorporeal fluid system. The gas data may for example be used for evaluating performance data of the oxygenation and the elimination of $CO_2$. Said parameters may then be used for setting the oxygenation using the blood flow and for setting the elimination of $CO_2$ using the gas rate.

In a further step, the gas sensor transmits the measurements data via a data line to an evaluation unit of the sensor device. The measurement data may be retrieved from the evaluation unit and may be reused for setting and enhancing the function of the medical extracorporeal fluid system.

The fluid is in particular blood, which is conducted from a vessel of a patient, which may be an artery or a vein, into a fluid line of the fluid system, wherein the blood may again be returned from the fluid system by a further fluid line into a blood vessel of the patient, which may be an artery.

Depending of the kind of the medical extracorporeal fluid system, introductory elements or discharge elements configured e.g. as cannulas may be introduced into the artery or vein, in order to discharge or introduce blood.

In an embodiment of the medical extracorporeal fluid system as medical extracorporeal blood circulation, in particular for an extracorporeal lung support (ECMO or ECLA), the access paths, by means of which blood is extracted from the patient and is returned to the patient, are the Vena femoralis and the Vena jugularis, for example.

In case of an extracorporeal lung support by a pump free extracorporeal lung support system (ILA or PECLA), the extraction of blood may be performed via the Arteria femoralis and the blood may be returned via the Vena femoralis.

A fluid line according to the invention is preferably any kind of line, which may be used in connection with a medical care, diagnosis or therapy, for example also in connection with any kind of catheters. The fluid line, which in particular contains blood, may be part of a so-called tubing set or may form said tubing set. The fluid line may for example be a tubing line, which is made of an at least partly elastic material. Preferably the fluid line is flexible and may also be formed in a resilient or elastic way. In particular, the fluid line may be curved or bent. The diameter of the fluid line may substantially be selected without any restriction. In particular, outer diameters of ⅜ inch or ¼ inch are advantageous, for example.

The wall of the fluid line or also the complete fluid line may be formed of a flexible plastic material, in particular of polyvinylchloride (PVC) material. Preferably, the plastic material is a soft PVC, which is free of phthalates and has a high purity. In the simplest case it is a tubing line, for example a PVC tube, which is often used in medical engineering. A thickness of the wall and/or fluid line is thus e.g. in the range of 1 mm to 5 mm, preferably in the range of 1.2 mm to 3.5 mm, more preferred in the range of 1.5 mm to 3 mm, in particular preferred in the range of 1.6 mm to 2.4 mm.

The intermediate element is preferably made of a plastic material, in particular adapted as plastic mould part. As material for the intermediate element polycarbonate is used, for example.

BRIEF DESCRIPTION OF THE DRAWINGS

The invention will be explained in greater detail in the following figures by means of exemplary embodiments. Regarding the description, in case individual reference numbers will not be described explicitly, reference is made to FIG. 1 or to the other figures. Illustrated are in.

DETAILED DESCRIPTION OF THE INVENTION

Figure 1:
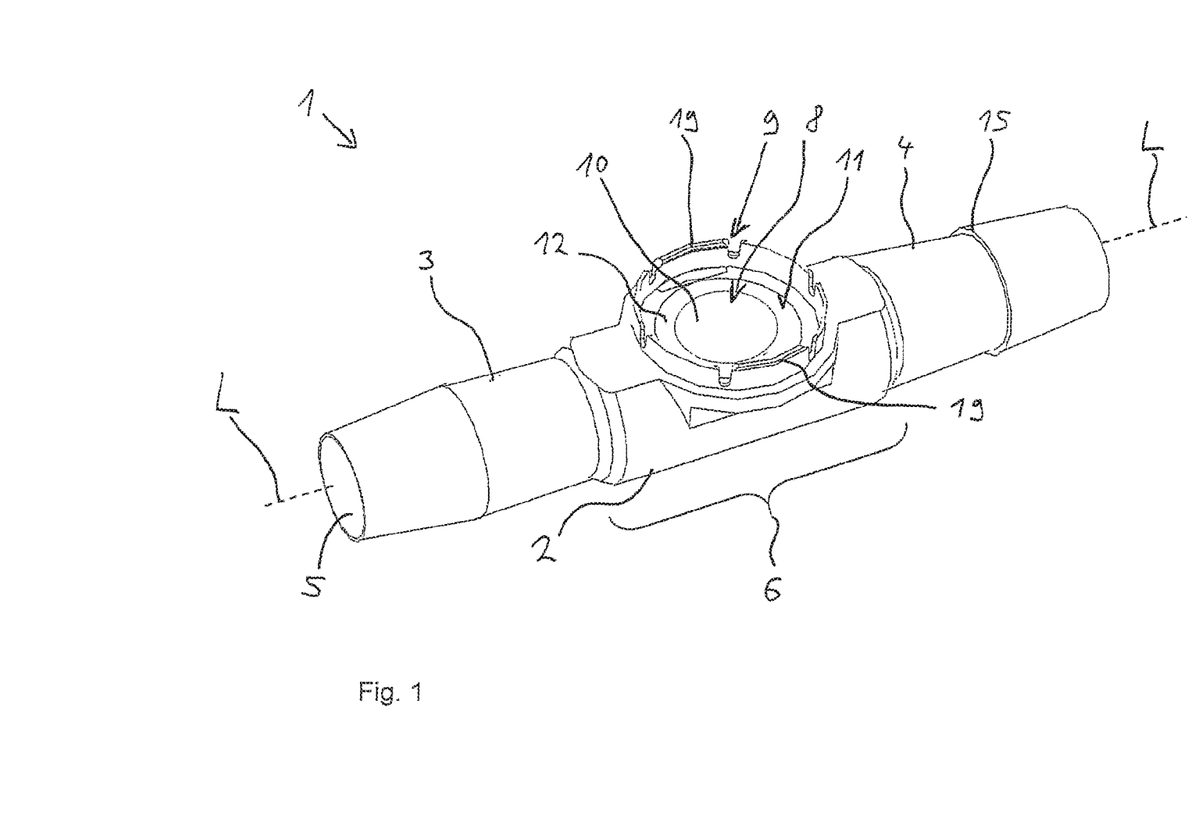
FIG. 1 a schematic representation in a perspective view of an intermediate element according to an exemplary embodiment of the invention.
Figure 2:
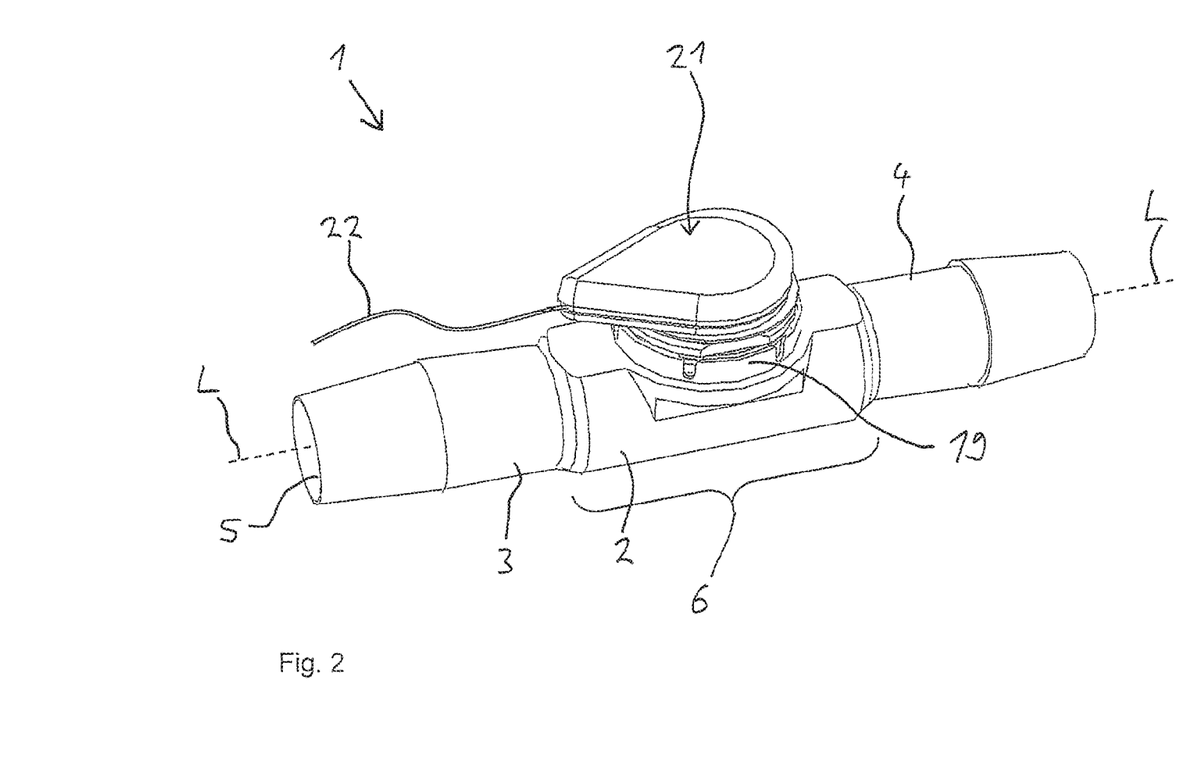
FIG. 2 a schematic representation in a perspective view of the intermediate element of FIG. 1 having a gas sensor, which is arranged in the receiving area of the intermediate element.
Figure 3:
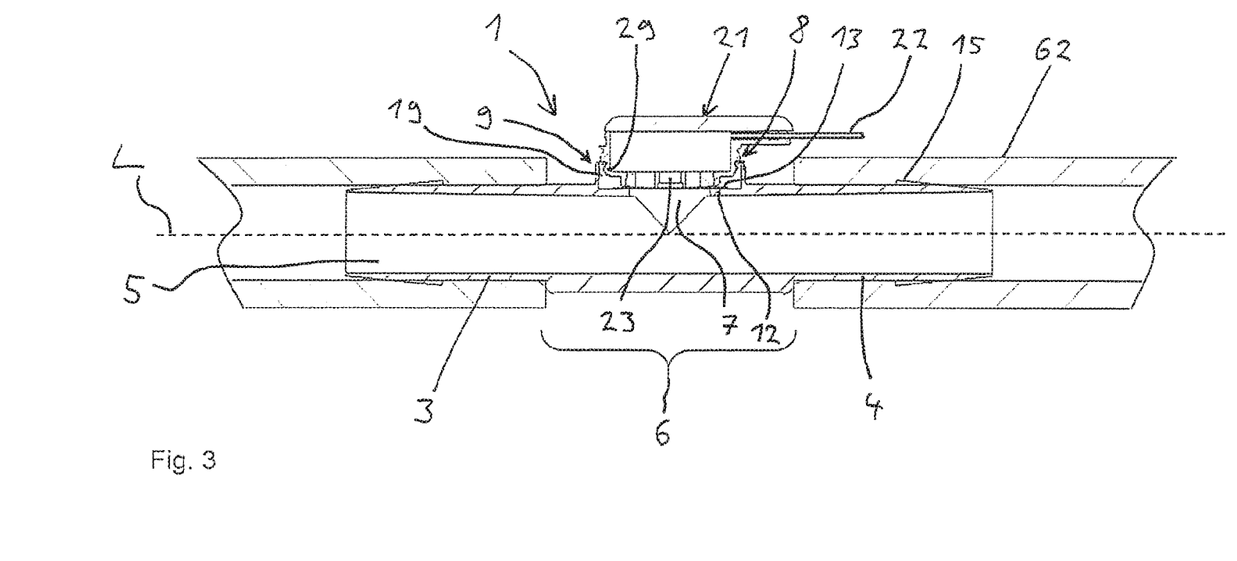
FIG. 3 a schematic section view of the intermediate element having a gas sensor, which is arranged thereon, in a section along line of FIG. 2.

In FIGS. 1 to 3 an intermediate element 1 according to the invention is shown for a medical extracorporeal fluid line 62 in an exemplary embodiment. In particular, the intermediate element 1 serves as a fluid-tight connection of two tube portions and has in total a longitudinal shape, which is aligned with a longitudinal axis L and comprises a main part 2, onto which connection parts 3, 4 are adjoining in both longitudinal directions of the longitudinal extension L. Here, the main part 2 forms a central portion 6. A receiving area 8 is arranged radially outside of the main part 2, which has a circular configuration in the exemplary embodiment and which is delimited radially outside by holder elements 19 of the holding device 9 for gas sensor 21, which is shown in FIGS. 2 and 3. The holder elements 19 of the holding device 9 are thus arranged around the receiving area 8 in an annular way.

A continuous flow channel 5 is passing through the main part 2 and the two connection parts 3 and 4 in the axial direction along the longitudinal extension L, which is delimited radially outside by a wall 14 in the main part 2 and the connection parts 3, 4. Here, the main part 2 has a radius remote from the receiving area 8, which at a maximum equals three times the inner radius of the flow channel 5. That is, the main part 2 is only insignificantly larger in a direction perpendicular to the longitudinal extension L thereof than the line portions or the tubing line portions of the fluid line 62, 64, which are to be connected hereby. In the region of the receiving area 8 an opening 7 is arranged in the main part 2 or the wall 14 at this position, which is clearly shown in particular in FIG. 3. Said opening, which is formed as a circular opening in the present exemplary embodiment, is closed towards the receiving area 8 by a diffusion element 10. The diffusion element 10 has a circular form in the present embodiment. The diffusion film or foil may also have a polygon geometry, in particular the shape of a n-cornered polygon, wherein n preferably may be in a range between 3-∞. The diffusion element 10 is bonded or fixed at a connection region 11, which is located radially outside, in particular by gluing or welding, by an annular edge region 13 of the diffusion element 10 on an also annular edge region 12, which in particular is formed as collar, at the main part 2 of the intermediate element 1. The bonded connection between the diffusion element 10 and the intermediate element 1 is absolutely fluid-tight. As displayed in FIGS. 2 and 3, a gas sensor 21 of a sensor device 20 may be set reversibly, that is detachable, on the receiving area 8. The holding device 9, already mentioned above, is used for setting the gas sensor 21 on the receiving area 8 in a reversible way, which in the present example comprises holder elements 19, which are arranged in an annular shape around the receiving area 8. Said holder elements 19 are formed as engagement hooks in the present embodiment, which may engage with counter holder elements 29 on the gas sensor 21, which are adapted as counter engagement elements. The holding device 9 acts here as a kind of engagement or snap connection, by means of which the gas sensor may be easily and rapidly set on the intermediate element 1 and may also be rapidly removed thereof. As is shown in particular in FIGS. 2 and 3, a measurement data line 22 is arranged on the gas sensor 21, by means of which the gas sensor 21 is connected to an evaluation unit 25 (only shown in FIGS. 4 and 5) and may transmit said measurement data to the sensor device 20 during operation. The diffusion element 10 is formed as a diffusion film or foil in the present embodiment and is made of poly-4-methyl-1-pentene. However, as an alternative, it may also be made of polypropylene or any other material, which is selected from the group of polymethyl-pentenes. In the present exemplary embodiment, the diffusion element 10 has a material thickness of 0.1 mm to 2.0 mm, preferably from 0.05 to ±0.01 mm. The intermediate element 1 itself is preferably made of a plastic material, for example of a plastic material selected from the group of polycarbonates.

The transition from the edge area 12 annularly surrounding the opening 7 to the diffusion element 10 is formed in the present example in way enabling a smooth flow of fluids, that is, there are no or only minor edges or steps in this transition region, which obstruct or impact the flow of a fluid flow in any way or may cause a turbulence. In addition, it is also prevented that deposits may occur in said transition region.

Both, the wall 14, in the complete region of the flow channel 5, and also the side of the diffusion element 10 facing the flow channel 5 may be provided with a coating in order to prevent or inhibit coagulation and/or immune responses.

The wall 14 delimiting the flow channel and/or the side of the diffusion element 10 facing the flow channel 5 may be coated with heparin, in particular with highly molecular heparin. Furthermore, an albumin coating may be provided alternatively or in addition, for example, in order to prevent an immune response. As mentioned above, also other coatings, which will be available in the future, may be provided.

As is shown in particular in FIG. 3, the bottom side of the gas sensor 21, that is the side facing the flow channel 5 or the diffusion element 10, abuts on the diffusion element 10 without any gap. Hereto, in the present exemplary embodiment, the diffusion element 10 is biased towards or pre-stressed the receiving area 8. By means of the biasing or prestressing a tight mechanical connection without any gap is generated between the diffusion element 10 and the gas sensor 21.

It is to be noted, that the gas sensor 21 projects the receiving area 8 only in the direction of the connection point of the measurement data line 22, but does not project the intermediate element 1 in the direction of the longitudinal extension L thereof. This eliminates the risk of unintentionally detaching the gas sensor 21 from the receiving area 8 or the intermediate element 1.

In FIG. 3 is shown as an example, how one end of the first fluid line 62 cooperates with a connection part 3 of the intermediate element 1. The end of the fluid line 62 is thus pushed on the connection part 3 from outside and is supported on the connection part 3 by a circumferential protrusion 15.

Figure 4:
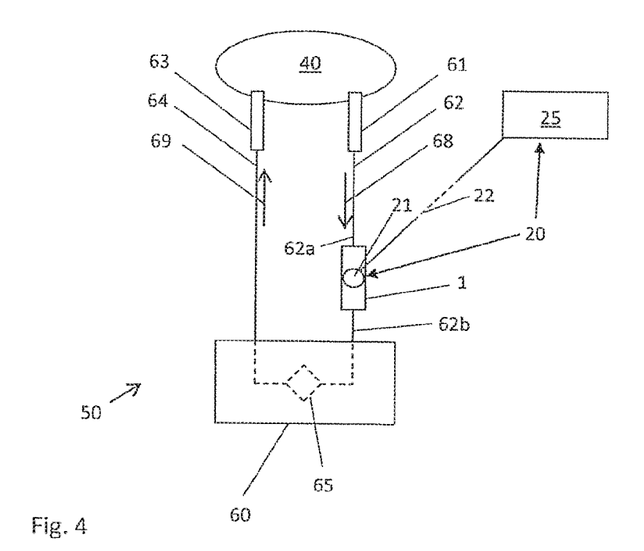
FIG. 4 a schematic representation of a medical extracorporeal fluid system.

In FIG. 4 a first exemplary embodiment of a medical extracorporeal fluid system 50 is shown, which is designed as pump-free arterio-venous lung support system (PECLA) or as interventional extracorporeal lung support (ILA), for example. Such systems provide extracorporeal blood circulations, in which a fluid, that is blood, is extracted from the body of a patient 40, is conducted through a gas exchange module 60 and is then returned to the patient 40 again. In the gas exchange module 60 $CO_2$ is extracted from the fluid or blood and at the same time the blood is oxygenated with oxygen or $O_2$. In the medical extracorporeal fluid system 50 shown in FIG. 4, a fluid, that is blood, is extracted from a patient 40 by means of an introduction element 61, which is in particular formed as a cannula, and is introduced into a first fluid line 62. Said first fluid line 62 comprises a first line portion 62a and a further line portion 62b. The first line portion 62a extends from the introduction element 61 to an intermediate element 1 according to the invention, which is connected to the first fluid line 62 by means of the connection parts 3 and 4, shown in FIGS. 1 to 3, to both free ends of the line portions 62a and 62b. That is, a flow of blood in the flow direction 68 goes from the first line portion 62a of the first fluid line 62 through the intermediate element 1 into the second line portion 62b of the first fluid line 62 to a gas exchange element 65 in the gas exchange module 60. Said gas exchange element 65 may be an oxygenator, for example. By means of the gas sensor arranged on the intermediate element, as shown in particular in FIGS. 2 and 3, the partial pressure of at least one gas selected from the group of $O_2$, $CO_2$, CO, $N_2$ is measured in the fluid or in the blood during operation of the medical extracorporeal fluid system 50. From the partial pressure data, the concentration of the gases in the fluid or blood may be determined.

A further fluid line 64 is extending from the gas exchange element 65, which on the end opposite to the gas exchange element 65 is connected to a discharge element 63, as for example a cannula, by means of which the fluid, that is the blood, which is returned into the fluid line 64 in the flow direction 69, is returned to the body of the patient 40. Here, the discharge element 63 is in particular introduced in a vein, in particular the Vena femoralis. The introduction element 61 is however preferably introduced in an artery, in particular the Arteria femoralis. However, $CO_2$ and $O_2$ may be in general measured in veins and arteries.

Figure 5:
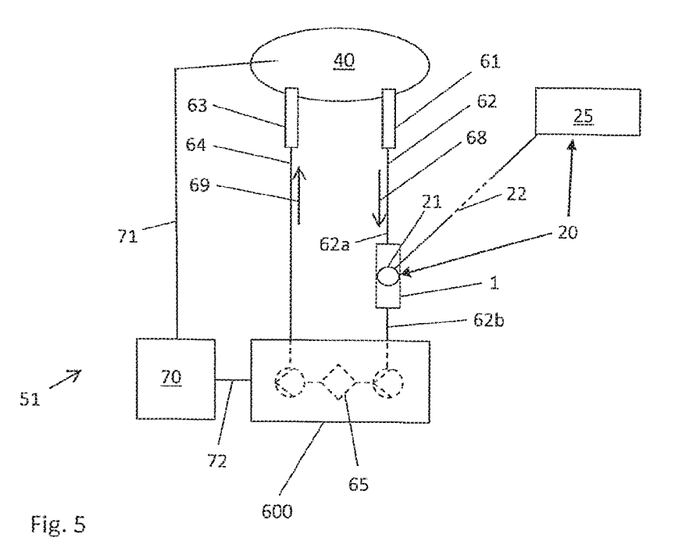
FIG. 5 a schematic representation of a further medical extracorporeal fluid system.

In FIG. 5 a further medical extracorporeal fluid system 51 is shown. The fluid system 51 shown is a system for the extracorporeal circulation support or extracorporeal life-support (ECLS), for example. Also, in this medical extracorporeal fluid system 51 a fluid, that is blood, is taken from a patient 40 by means of an introduction element 61, which is in particular formed as a cannula, and is introduced into a first fluid line 62. Said first fluid line 62 comprises a first line portion 62a and a further line portion 62b. Here, the first line portion 62a extends from an introduction element 61 to an intermediate element 1 according to the invention, which is connected by means of the connection parts 3 and 4, shown in FIGS. 1 to 3, by both free ends of the line portions 62a and 62b to the first fluid line 62. As in the exemplary embodiment of FIG. 4, here a flow of blood is also conducted in the flow direction 68 from the first line portion 62a of the first fluid line 62 through the intermediate element 1 into the second line portion 62b of the first fluid line. In the present exemplary embodiment, in addition to the gas exchange element 65, the gas exchange module 600 comprises also a pump 66 to which the second line portions 62b of the first fluid line 62 is routed. Said pump 66 is then hydraulically connected to the gas exchange element 65, as for example an oxygenator, by means of a further line. An additional pump 67 is arranged downstream of the fluid circuit after the gas exchange element 65, which is connected to the further fluid line 64 on the side of the pump outlet in order to pass the fluid in the flow direction 69 to the discharge element 63, as for example a cannula, and to return it to the patient 40. In said medical extracorporeal fluid system 51, a control unit 70 is also provided, which is connected to the gas exchange module 600 by means of a line 72, which is designed to perform control, and by means of which the pump performance of the pumps 66 and 67 is controlled. By means of a further line 71, the control unit is connected to an ECG (electro-cardiogram, electrocardiography), which provides a control signal to the control unit 70.

In pump systems also a veno-veneous variant is possible, for example in a veno-veneous extracorporeal membrane oxygenation (VV-ECMO). This is for example achieved by a multiple or double lumen cannula, for example in the Vena jugularis. Thereby, a measurement upstream and downstream of the gas exchange element would be possible anyway.

The intermediate element may also be formed as an oxygenator and include a sensor, for example.

LIST OF REFERENCE NUMBERS

1 Intermediate element
2 Main part
3 Connection part
4 Further connection part
5 Flow channel
6 Central portion
7 Opening
8 Receiving area (for gas sensor)

9 Holding device (for gas sensor)
10 Diffusion element
11 Connection region of 10 to 1
12 Edge region (collar)
13 Edge region of 10
14 Wall
15 Protrusion
19 Holder elements
20 Sensor device
21 Gas sensor
22 Measurement data line
23 Input opening of 20
24 Sensor element
25 Evaluation unit
29 Counter holder element
40 Patient
50 Fluid system
51 Further fluid system
60 Gas exchange module
61 Introduction element (canula)
62 First fluid line
62a First line portion
62b Further line portion
63 Discharge element (canula)
64 Further fluid line
65 Gas exchange element
66 Pump
67 Further Pump
68 Flow direction
69 Flow direction
70 Control unit
71 Line (for ECG)
72 Line (70 to 60)
600 Further gas exchange module
L Longitudinal axis

The invention claimed is:

1. An intermediate element for a medical extracorporeal fluid line, which is configured to conduct a fluid, the intermediate element comprising:
 a main part which extends between connection parts, the connection parts configured to connect the main part to a fluid line for conducting a fluid;
 a flow channel passing continuously through the main part and connection parts for conducting the fluid;
 a receiving area arranged on the periphery of the main part and being integral with the main part, the receiving area configured to receive a measurement value transmitter of a sensor device, which is designed as a gas sensor for measuring at least one gas contained in the fluid, an opening to the flow channel defined in the receiving area; and
 an elastic element sealing the opening in a fluid-tight manner, the elastic element being a diffusion element, which is permeable for at least one gas, the diffusion element being bonded directly to an edge of the opening in the receiving area.

2. The intermediate element according to claim 1, wherein the diffusion element is a diffusion film or foil having a circular geometry.

3. The intermediate element according to claim 1, wherein the diffusion element is formed of a material selected from a group of polymethyl-pentenes, poly-4-methyl-1-pentenes, and polypropylenes.

4. The intermediate element according to claim 1, wherein at least a wall of the flow channel is provided with a coating in order to prevent or inhibit coagulation and/or immune responses.

5. The intermediate element according to claim 1, wherein the diffusion element is provided with a coating at least on a side facing the flow channel in order to prevent or inhibit coagulation and/or immune responses.

6. The intermediate element according to claim 1, the diffusion element is biased or prestressed towards the receiving area.

7. The intermediate element according to claim 1, wherein a transition from the diffusion element to an adjacent portion of the wall of the flow channel is smooth to fluids.

8. The intermediate element according to claim 1, wherein a holding device is provided on the receiving area, the holding device being configured to set the gas sensor on the receiving area in a reversible way.

9. The intermediate element according to claim 8, wherein the holding device comprises at least one holder element designed to cooperate with a counter holder element of the gas sensor.

10. The intermediate element according to claim 8, wherein the at least one holder element is an engagement hook, adapted to cooperate with a counter holder element, which is an engagement protrusion.

11. The intermediate element according to claim 8, wherein the holding device comprises a plurality of holder elements, which are arranged on a periphery around the receiving area.

12. The intermediate element according to claim 1, wherein the intermediate element is configured as a disposable element, which is designed for single use only.

13. A medical extracorporeal fluid system for fluid circulation, comprising:
 at least one fluid line configured to conduct a fluid, the fluid line configured to be connected to an intermediate element according to claim 1 in such a way that the intermediate element is hydraulically interposed in the fluid line;
 at least one introduction element configured to conduct a fluid of the patient into the fluid line; and
 a gas exchange module, which is hydraulically connected to the at least one fluid line.

14. The medical extracorporeal fluid system according to claim 13, wherein a first of the at least one fluid line is connected to the introduction element and to the gas exchange module, the first fluid line adapted for hydraulic connection to the intermediate element.

15. The medical extracorporeal fluid system according to claim 14, wherein the first fluid line comprises two line portions which are separate from each other, an end of each of the line portions configured for connection to the intermediate element.

16. The medical extracorporeal fluid system according to claim 13, wherein the intermediate element is hydraulically interposed in a first one of the at least one fluid line.

17. A method for measuring a gas contained in human or animal bodily fluid conducted in a medical extracorporeal fluid system, comprising:
 providing an intermediate element according to claim 1;
 hydraulically interposing the intermediate element in a fluid line of a medical extracorporeal fluid system; and
 arranging a gas sensor of a sensor device on the receiving area of the intermediate element
 conducting a fluid of a patient in a first fluid line of the fluid system; and
 returning the fluid from the fluid system to the patient by a further fluid line;
 wherein the fluid flows through the flow channel of the intermediate element and is thus passed next to the diffusion element, which abuts the sensor element of the gas sensor on a side of the diffusion element opposite to the flow channel; and wherein the gas sensor measures a partial pressure of at least one gas contained in the fluid, which is selected from the group of $O_2$, $CO_2$, CO, and $N_2$.

18. The method according to claim 17, wherein the gas sensor transmits the measurement data by means of a data line to an evaluation unit of the sensor device.

19. The method according to claim 17, wherein:
the fluid is blood, which may be taken from a blood vessel of a patient, which may be an artery or a vein, which is conducted into the first fluid line of the fluid system; and the blood is returned from the fluid system by means of the further fluid line into a blood vessel of the patient, which may be an artery or vein.

20. The method according to claim 17, wherein the gas sensor is configured to measure the partial pressure of the gases $O_2$ and $CO_2$ in parallel.

21. The intermediate member according to claim 1, wherein the diffusion element is liquid impermeable.

22. The intermediate member according to claim 1, wherein the diffusion element being bonded directly to the edge of the opening in the receiving area comprises the diffusion element being directly bonded to the edge by welding or gluing.

* * * * *